United States Patent
Fredman et al.

(10) Patent No.: US 6,908,904 B2
(45) Date of Patent: Jun. 21, 2005

(54) PHARMACEUTICAL PREPARATION AND METHOD FOR TREATMENT OF DIABETES

(76) Inventors: Pam Fredman, Pilfinksgatan 4, SE-412 67 Göteborg (SE); Karsten Buschard, Kollegievej 5, DK-2920 Charlottenlund (DK)

( * ) Notice: Subject to any disclaimer, the term of this patent is extended or adjusted under 35 U.S.C. 154(b) by 0 days.

(21) Appl. No.: 10/200,131

(22) Filed: Jul. 23, 2002

(65) Prior Publication Data

US 2003/0004115 A1 Jan. 2, 2003

Related U.S. Application Data

(63) Continuation-in-part of application No. PCT/SE01/00169.

(30) Foreign Application Priority Data

Jan. 27, 2000 (SE) ................................................ 0000258

(51) Int. Cl.[7] ......................... A01N 43/04; A61K 31/70; A61K 31/715
(52) U.S. Cl. ............................. 514/25; 514/53; 514/54; 514/866
(58) Field of Search ............................. 514/25, 53, 54, 514/866

(56) References Cited

U.S. PATENT DOCUMENTS

| 5,302,609 | A |   | 4/1994 | Shayman et al. |
| 5,827,828 | A | * | 10/1998 | Buschard et al. |
| 6,352,831 | B1 | * | 3/2002 | Buschard et al. ............ 435/7.1 |

FOREIGN PATENT DOCUMENTS

| EP | 0 988 860 |   | 3/2000 |
| WO | 92/19633 |   | 11/1992 |
| WO | 98/30573 |   | 7/1998 |
| WO | 98/44928 |   | 10/1998 |
| WO | 99/33475 |   | 7/1999 |
| WO | 01/54700 |   | 8/2001 |

OTHER PUBLICATIONS

"Prediabetes", The American Heritage Dictionary of the English Language Online Edition: 4th Edition, 2000.*
Diabetologia, vol. 42, 1999, K. Buschard et al., "Inhibition of insulin–specific autoreactive T–cells by sulphatide which is variably expressed in beta cells" pp. 1212 to 1218.
Dialog Information Services, File 73, EMBASE, Dialog accession No. 6116895, EMBASE accession No. 1995147628, Buschard K. et al., "Neonatal treatment of BB rats with sulphatide delays development of diabetes but does not change incidence" (APMIS), (Denmark) 1995, 103/3 (193–196).

* cited by examiner

Primary Examiner—James O. Wilson
Assistant Examiner—Traviss C. McIntosh, III
(74) Attorney, Agent, or Firm—Burns, Doane, Swecker & Mathis, LLP

(57) ABSTRACT

A method for treatment of a diabetic condition, wherein a therapeutically effective amount of at least one isoform of sulfatide is administered to a patient, wherein said at least one isoform of sulfatide upon administration to the patient affects the sulfatide metabolism in such a way that it results in an increased amount of sulfatide.

Also the use of at least one isoform of sulfatide for the production of a pharmaceutical preparation for treatment of a diabetic condition is disclosed.

Said isoform is preferably an isoform with 8–24 carbon atoms in the fatty acid chain, more preferably 12, 14, 16 or 18 carbon atoms, and most preferably 16 carbon atoms.

27 Claims, 15 Drawing Sheets

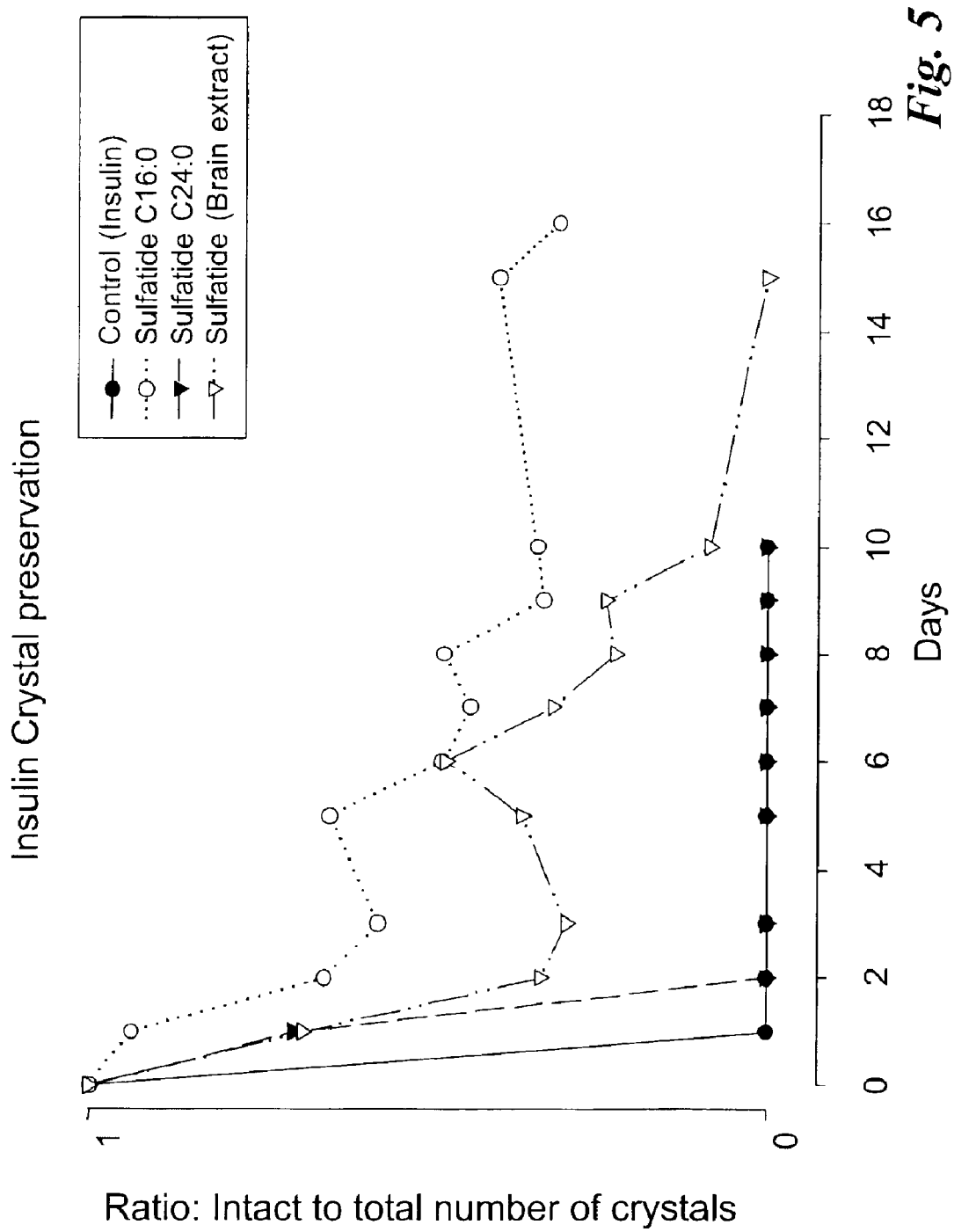

PHARMACEUTICAL PREPARATION AND METHOD FOR TREATMENT OF DIABETES

CONTINUATION APPLICATION DATA

This application is a Continuation-in-Part Application of International Application No. PCT/SE01/00169, filed in English on Jan. 29, 2001, which claims benefit of Swedish Application No. 0000258-4 filed on Jan. 27, 2000. The International Application was published in English on Aug. 2, 2001.

DESCRIPTION

1. Field of the Invention

The present invention relates to new methods and pharmaceutical preparations for treatment of diabetes, in particular diabetes type 2.

2. Background of the Invention

Diabetes is a very common disease in which the body does not produce any or enough insulin or does not properly use insulin. There are two major types of diabetes: diabetes type 1, or insulin-dependent diabetes mellitus (IDDM), in which the body does not produce any insulin, most often manifesting in children and young adults and regarded as an autoimmune disease; and diabetes type 2, noninsulin-dependent diabetes mellitus (NIDDM) the most common form of the disease, which is a metabolic disorder resulting from the body's inability to make enough, or properly use, insulin. Diabetes type 2 accounts for approximately 90% of all cases of diabetes. It is also a very common disorder, affecting 2–10% of the population in the Western world. The causes of diabetes type 2 are not completely known, though both genetic and environmental factors, such as obesity and lack of exercise, appear to play roles. There is also a form of diabetes that women may develop during pregnancy, gestational diabetes, and a form of autoimmune diabetes with starts in adult-hood, which is called LADA (latent autoimmune diabetes in adults) or slowly progressing autoimmune diabetes.

Diabetes type 1 is generally treated with insulin. Other possible ways to treat in particular diabetes type 1 have been described i.a. in WO 92/19633, which relates to the use of sulfated glycolipids, WO 97/42974, which relates to the use of glycolipid complexes, and WO 99/33475, which relates to the use of galactosylceramide, glucosylceramide, and lactosylceramide.

Also transplantation of pancreas or insulin producing pancreatic cells has been tested.

Diabetes type 2 is normally first treated with special diets, and if this is not enough then generally treated with one of three different types of drugs; either a drug that stimulates the release of insulin from pancreas, or a drug that increases the patient's sensitivity to insulin, or a drug that directly affects the blood level of glucose (such as drugs decreasing the production of glucose form the liver or drugs increasing the uptake of glucose into muscles). These drugs may also be used in combination with different diets. In many cases also insulin is used.

None of the current treatment strategies is applicable with optimal results for all diabetic patients and there is thus a great demand for efficient ways to treat diabetes, and especially diabetes type 2.

SUMMARY OF THE INVENTION

The object of the invention is thus to provide a new way to treat diabetes, particularly diabetes type 2.

In the work leading to the present invention it was found that sulfatide is an important substance in the prevention and treatment of diabetes, and especially diabetes type 2.

The invention is thus based on this finding. It has been shown that the use of at least one substance that upon administration to a patient will affect the sulfatide metabolism in a way that leads to an increased amount of sulfatide, or, more precisely, at least one molecular species or isoform of sulfatide, can be used in a method for treatment of a diabetic condition and for the production of a pharmaceutical preparation for treatment of a diabetic condition.

The invention thus relates to a method and a pharmaceutical preparation for treatment of a diabetic condition, wherein a therapeutically effective amount of a substance that upon administration to a patient affects the sulfatide metabolism in such a way that it results in an increased amount of sulfatide, or more precisely, at least one molecular species or isoform of sulfatide, wherein said substance is an isoform of sulfatide.

Furthermore, it was found that specific isoforms, namely the isoforms with 8–24 carbon atoms in general, and in particular the isoforms with 12–18, and even more particular the isoforms with 12, 14, or 16 carbon atoms, and most particular the isoform with 16 carbon atoms, in the fatty acid chain lead to an increased uptake of sulfatide.

One embodiment of the invention is thus a method for treatment of a diabetic condition, such as pre-diabetes; diabetes, e.g. diabetes type 1, diabetes type 2, LADA and/or gestational diabetes; glucose intolerance, insulin resistance and/or a complication associated with diabetes, wherein a therapeutically effective amount of the isoform of sulfatide having 12 carbon atoms in its fatty acid chain is administered to a patient.

Another embodiment of the invention is thus a method for treatment of a diabetic condition, such as pre-diabetes; diabetes, e.g. diabetes type 1, diabetes type 2, LADA and/or gestational diabetes; glucose intolerance, insulin resistance and/or a complication associated with diabetes, wherein a therapeutically effective amount of the isoform of sulfatide having 14 carbon atoms in its fatty acid chain is administered to a patient.

Another embodiment of the invention is thus a method for treatment of a diabetic condition, such as pre-diabetes; diabetes, e.g. diabetes type 1, diabetes type 2, LADA and/or gestational diabetes; glucose intolerance, insulin resistance and/or a complication associated with diabetes, wherein a therapeutically effective amount of the isoform of sulfatide having 16 carbon atoms in its fatty acid chain is administered to a patient.

Another embodiment of the invention is thus a method for treatment of a diabetic condition, such as pre-diabetes; diabetes, e.g. diabetes type 1, diabetes type 2, LADA and/or gestational diabetes; glucose intolerance, insulin resistance and/or a complication associated with diabetes, wherein a therapeutically effective amount of the isoform of sulfatide having 18 carbon atoms in its fatty acid chain is administered to a patient.

Another embodiment of the invention is the use of the isoform of sulfatide having 12 carbon atoms in its fatty acid chain for the production of a pharmaceutical preparation for treatment of a diabetic condition, such as pre-diabetes; diabetes, e.g. diabetes type 1, diabetes type 2, LADA and/or gestational diabetes; glucose intolerance, insulin resistance and/or a complication associated with diabetes.

Another embodiment of the invention is the use of the isoform of sulfatide having 14 carbon atoms in its fatty acid chain for the production of a pharmaceutical preparation for treatment of a diabetic condition, such as pre-diabetes; diabetes, e.g. diabetes type 1, diabetes type 2, LADA and/or gestational diabetes; glucose intolerance, insulin resistance and/or a complication associated with diabetes.

Another embodiment of the invention is the use of the isoform of sulfatide having 16 carbon atoms in its fatty acid chain for the production of a pharmaceutical preparation for treatment of a diabetic condition, such as pre-diabetes; diabetes, e.g. diabetes type 1, diabetes type 2, LADA and/or gestational diabetes; glucose intolerance, insulin resistance and/or a complication associated with diabetes.

Another embodiment of the invention is the use of the isoform of sulfatide having 18 carbon atoms in its fatty acid chain for the production of a pharmaceutical preparation for treatment of a diabetic condition, such as pre-diabetes; diabetes, e.g. diabetes type 1, diabetes type 2, LADA and/or gestational diabetes; glucose intolerance, insulin resistance and/or a complication associated with diabetes.

The diabetic conditions that may be treated according to the present invention includes pre-diabetes, diabetes, glucose intolerance, insulin resistance and complications associated with diabetes. The diabetes treatable according to the present invention includes diabetes type 1, diabetes type 2, LADA and gestational diabetes.

The pharmaceutical composition produced according to the invention and the method according to the invention are thus suitable for treatment of a diabetic condition, such as prediabetes, diabetes and/or a complication associated with diabetes.

The characterizing features of the invention will be evident from the following description and the appended claims.

BRIEF DESCRIPTION OF THE DRAWINGS

In the detailed description and the examples below, reference is made to the accompanying drawings on which:

FIG. 5 illustrates that the isoform of sulfatide with 16 carbon atoms in the fatty acid has a significant effect on the preservation of insulin crystals as compared to the C24 analogue and to native sulfatide, as well as to insulin stored without sulfatide;

DETAILED DESCRIPTION OF THE INVENTION

As stated above, the inventors have found that sulfatide is an important substance in prevention of diabetes, and especially diabetes type 2.

Figure 1:
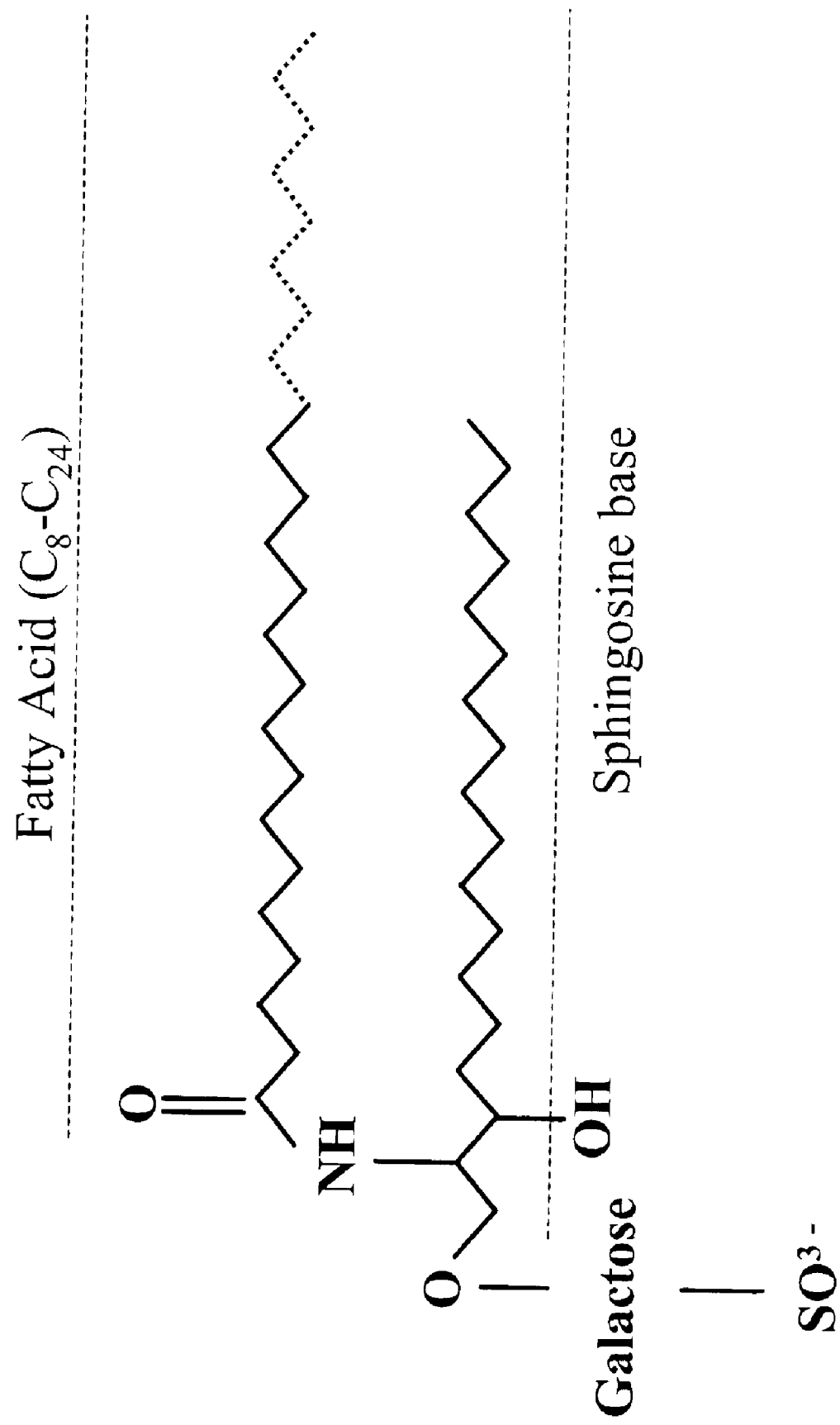
FIG. 1 is a schematic illustration of a sulfatide molecule.

Sulfatide, or galactosylceramide-3-O-sulfate, is an acidic glycosphingolipid. A schematic illustration of the sulfatide molecule is shown in FIG. 1. As seen in the figure, the sulfatide molecule comprises a sulfated galactose, a sphingosine base, and a fatty acid. A variety of molecular species of sulfatide, or sulfatide isoforms, have earlier been described, and they differ from each other in the number of carbons present in the fatty acid and in the degree of unsaturation and hydroxylation.

The different sulfatide isoforms have, to some extent, different biological activities. Furthermore, some cases of diabetes type 2 may be due to lack of a specific molecular species, or isoform, of sulfatide, and it may then be important to perform the treatment according to the invention in such a way that an increased amount of this specific molecular species is obtained.

According to the present invention it is possible to use all different isoforms of sulfatide, both naturally occurring and synthetic.

According to the invention the use of sulfatide isoforms with 8–24, preferably 12, 14 or 16 carbon atoms in the fatty acid chain are preferred, and especially preferred is the sulfatide isoform with 16 carbon atoms in the fatty acid chain, since this isoform leads to the best uptake of sulfatide, as illustrated further in the examples below.

Sulfatide is produced in the insulin producing cells in a variety of mammalian species, including man and it has been found that there is an isoform specific for these cells. The fact that sulfatide is processed through the same intracellular route as insulin further supports the findings according to the invention. Sulfatide is involved in normal processing of insulin, from proinsulin to secreted monomeric insulin. It is involved in the folding and oxidation of proinsulin, and is thus required for insulin formation, it is involved in the preservation of insulin crystals in secretory granules, and is thus required for the storage of the insulin pool, prevents deterioration and fibril formation, and it is involved in the transformation of insulin from hexamer via dimer to monomer form at secretion, and this last conversion to monomer is required for biological activity. Furthermore, sulfatide might be needed in combination with insulin in order to affect the insulin receptors in a proper way and to avoid development of insulin resistance. The inventors of the present invention have found that sulfatide in combination with insulin inhibited the T-cell response to insulin supporting that sulfatide and insulin are normally complexed in the circulation and as such does not induce immune response seen in diabetes type 1 patients and in response to exogenously administrated insulin.

An altered sulfatide synthesis is thus a pathogenic factor involved in diabetes, both diabetes type 1 and diabetes type 2. The inventors have for example shown that a deficient sulfatide metabolism is associated with insulin deficiency (this is further illustrated in the example) as well as in insulin resistance in diabetes type 2.

Figure 2:
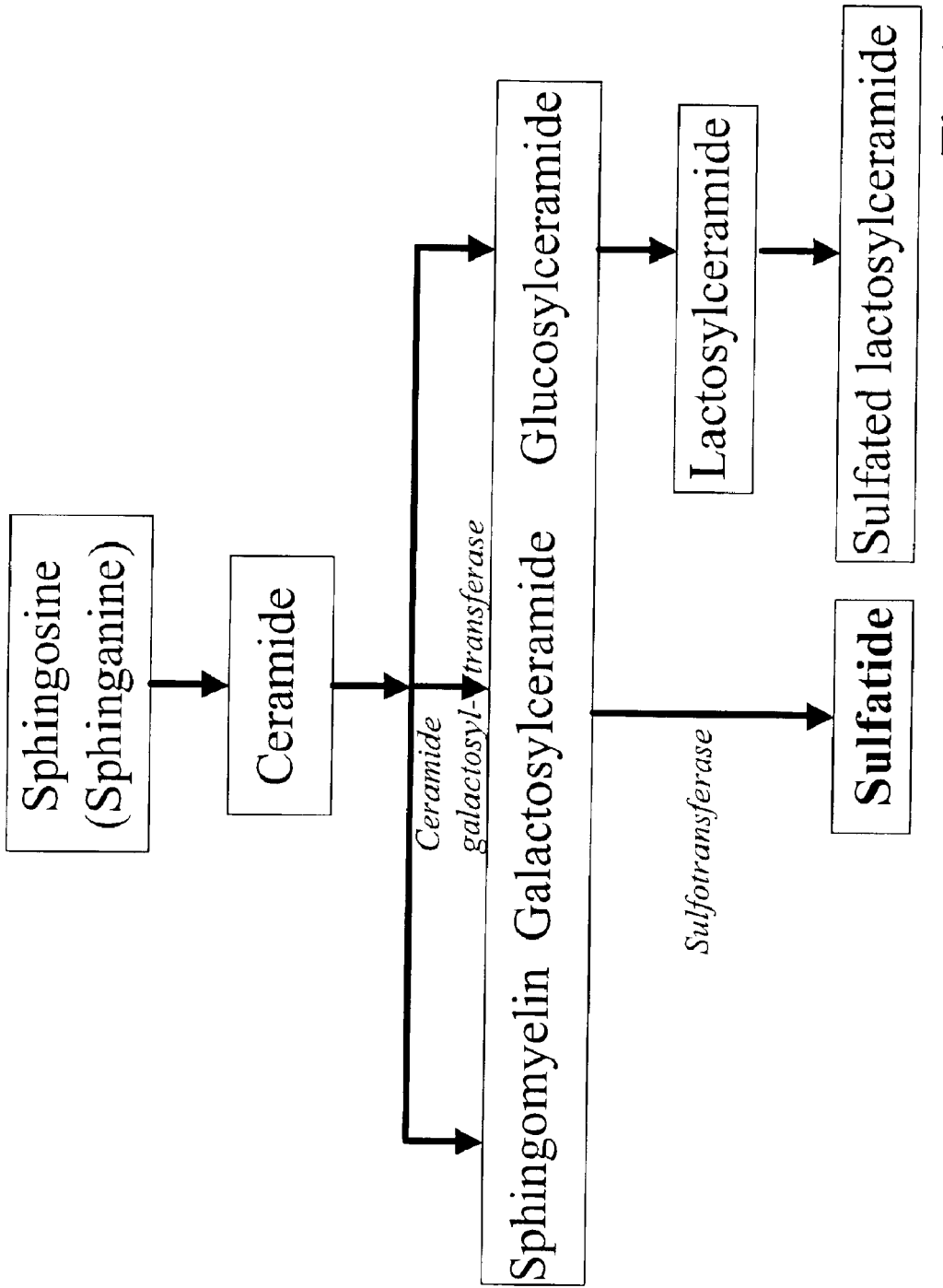
FIG. 2 illustrates the metabolism of sulfatide.

Sulfatide metabolism occurs i.a. in the Golgi complex of islets of Langerhans in pancreas. A schematic illustration of the sulfatide metabolism is shown in FIG. 2. As seen in the figure, this metabolic pathway involves several steps. In order to obtain the result desired according to the present invention, i.e. to obtain an increased amount of at least one molecular species of sulfatide, it is possible to affect this pathway by affecting the level of the end product sulfatide. This may be done. It is possible to affect the level of sulfatide by the administration of an isoform of sulfatide, or functionally equivalent analogues thereof. The isoform may be either one of or a combination of the isoforms wherein the fatty acid part comprises 8–24, preferably 12, 14 or 16, and most preferably 16 carbons, or functionally equivalent analogues thereof, and, as stated above and further commented on below, in some cases it may be preferable to administer one specific molecular species or isoform of sulfatide, i.e. an isoform with a specific number of carbons.

The expression "treatment" used herein relates to both therapeutic treatment, i.e. treatment in order to cure or alleviate a disease or a condition, and to prophylactic treatment, i.e. treatment in order to prevent the development of a disease or a condition. The treatment may either be performed in an acute or in a chronic way.

The expression "patient" used herein relates to any human or non-human mammal in need of treatment according to the invention. The expression also includes persons with pre-diabetes, insulin resistance and/or glucose intolerance, although such persons are not considered as patients in other contexts.

The expression "functionally equivalent analogue" used herein relates to a substance that will have essentially the same biological effect as the substance it is an analogue of within the meaning of the present invention. A functionally equivalent analogue of an isomer of sulfatide is thus a substance that will have essentially the same effect on insulin as the sulfatide isomer.

The expression "therapeutically effective amount" used herein relates to an amount that will lead to a therapeutical effect.

The pharmaceutical preparation according to the invention may also comprise substances used to facilitate the production of the preparation it self, or facilitate the administration of the preparation. Such substances are well known to man skilled in the art, and may for example be pharmaceutically acceptable adjuvants, carriers, and preservatives.

The pharmaceutical preparation and the method according to the invention are also suitable for prevention and/or treatment of different diseases associated with and/or due to diabetes. Such associated diseases may for example be diseases affecting eyes, kidneys and nerves, as well as heart and blood vessel diseases.

EXAMPLE 1

This example illustrates that a deficient sulfatide metabolism is associated with insulin deficiency.

Lipids were extracted from islets cell isolated from pancreatic tissue from Ob/Ob mice and Lewis rats. The lipid extracts were separated and analyzed by thin-layer chromatography combined with immunohistochemical analyses using a sulfatide specific monoclonal antibodies. Sulfatide standards of known amounts were analyzed in parallel to allow quantification. The obtained quantitative values for sulfatide in islet cells from the mice are shown in Table 1 below. The results showed a marked reduction of the total amount of sulfatide in the islets from the diabetes type 2 model.

TABLE 1

| Species | Sulfatide (pmol/mg protein) | Sulfatide (pmol/islet) |
|---------|------------------------------|------------------------|
| Ob/Ob   | 0.1                          | 0.1                    |
| Lewis   | 3–5                          | 1–2                    |

Figure 3:
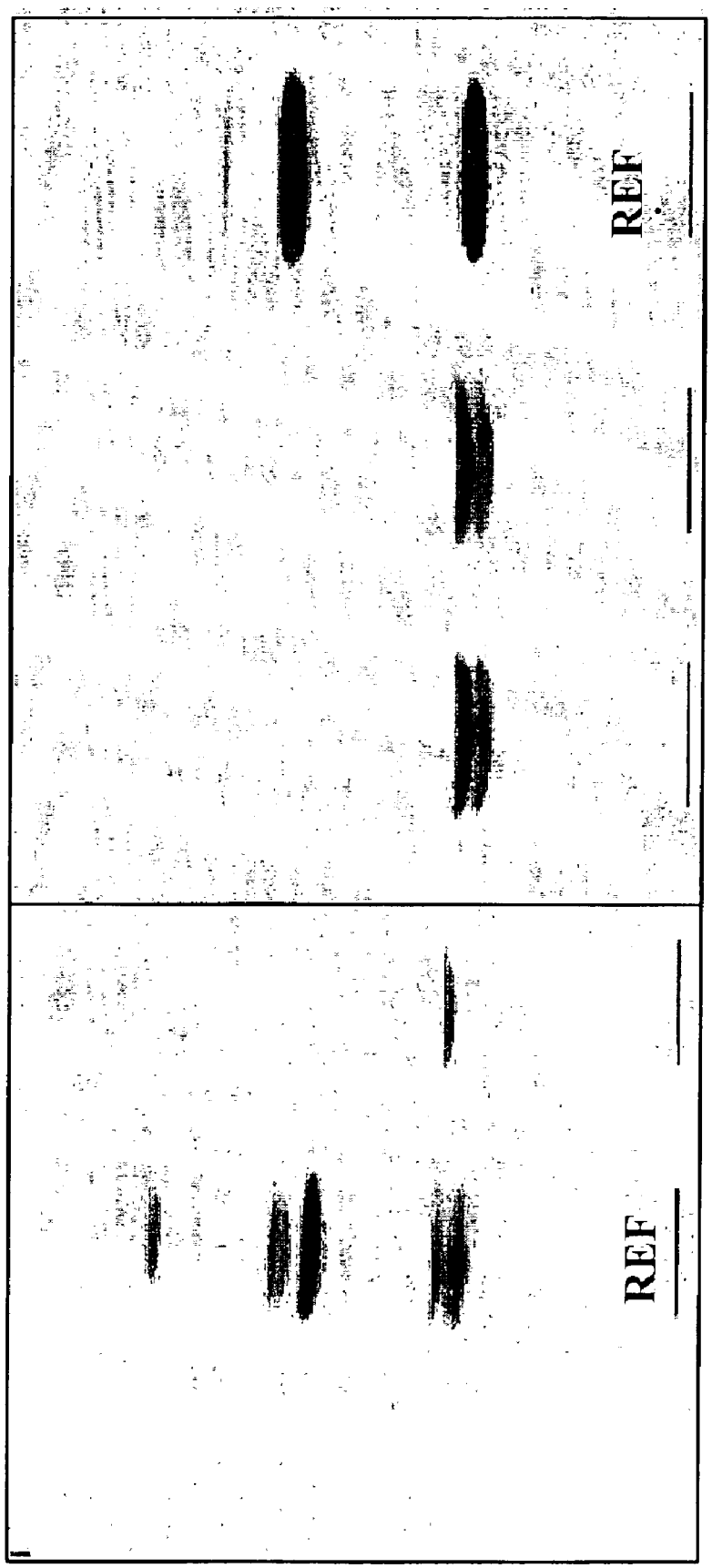
FIG. 3 is an autoradiogram revealing a lipid moiety difference between sulfatide from Lewis rats and the Ob/Ob mice.

Islets cell isolated from pancreatic tissue from Ob/Ob mice and Lewis rats were grown in media containing $^{35}$S-sulfate. The lipids were then extracted, separated and analyzed autoradiography after chromatography on silica gel thin layer plates. FIG. 3 shows the autoradiogram and reveal a lipid moiety difference between sulfatide from Lewis rats and the Ob/Ob mice, a diabetes type 2 model.

EXAMPLE 2

Studies on the Uptake of Sulfatide in Pancreas and Liver in ob/ob Mice after Intraperitoneal Injection This example illustrates that the sulfatide isoform with a fatty acid chain having 16 carbon atoms optimizes the uptake of sulfatide and the insulin processing.

In this example the expression "Cn:x analogue" denotes the isoform of sulfatide with n carbon atoms and x double bonds, for instance the C8:0 analogue is thus the isoform of sulfatide with 8 carbon atoms and no double bonds in its fatty acid chain.

Background

Figure 4:
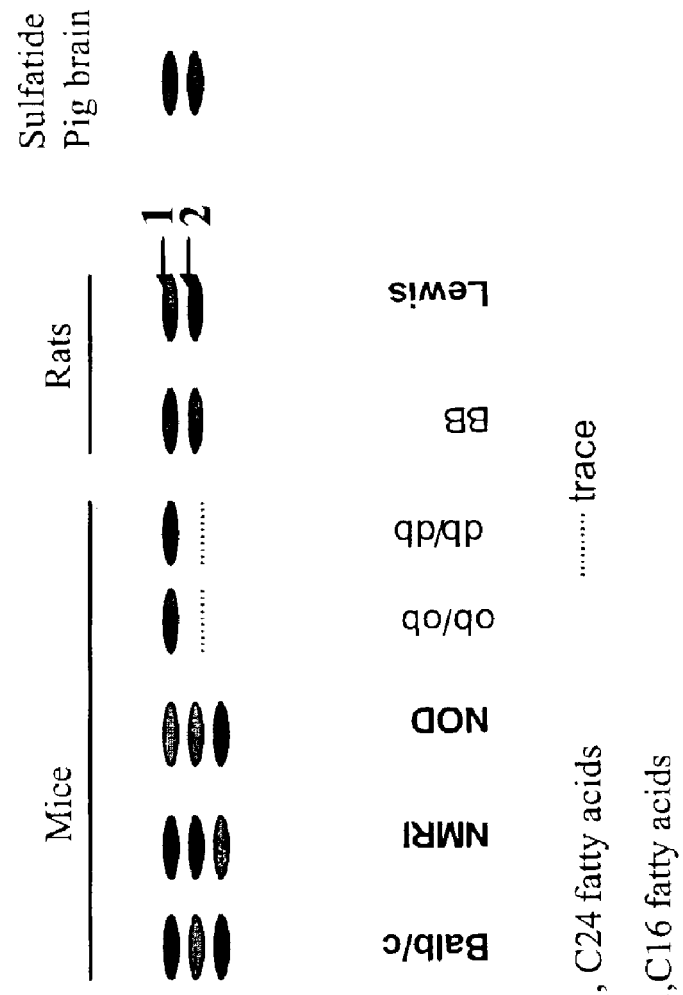
FIG. 4 illustrates that there are two major analogues, one with C24:0 fatty acid and one with C16:0 fatty acid in islets of Langerhans from pancreas of Lewis rats and BB rats, and that the C16:0 analogue is reduced to undetectable concentration in the two type 2 mice models ob/ob and db/db (as studied with TLC-ELISA using a anti-sulfatide monoclonal antibody)

Ob/ob mice have by biochemical analyses been shown to have an aberrant sulfatide metabolism, both quantitatively and qualitatively (see Example 1). Sulfatide is a sulfated glycosphingolipid in which the composition of the lipid moiety may vary. In islets of Langerhans from pancreas of Lewis rats and BB rats there are two major analogues, one with C24:0 fatty acid and one with C16:0 fatty acid. In the two type 2 mice models ob/ob and db/db the C16:0 analogue is reduced to undetectable concentration (as studied with TLC-ELISA) using a anti-sulfatide monoclonal antibody. This is shown in FIG. 4.

The inventors have performed in vitro studies that reveals that the C16:0 analogue is important for the insulin processing. The preservation of insulin crystals, a requirement for storage of an insulin pool that can be released upon raised blood glucose, is increased for sulfatide C16:0 compared to other sulfatide isoforms. The C16:0 analogue of sulfatide has a significant effect on the preservation as compared to the C24:0 analogue and to native mixture of sulfatide from pig brain, as well as to insulin stored without sulfatide. This is illustrated in FIG. 5.

Hypothesis

The lack of C16:0 analogue of sulfatide in islets of Langerhans of the diabetes type 2 models leads to non-optimal insulin processing. This might effect not only insulin deficiency but also insulin resistance. Restoration of the presence of C16:0 sulfatide in the islets by providing C16:0 sulfatide is thus a strategy to treat diabetes type 2.

Experimental Design

Native sulfatide isolated from pig brain and structurally characterized by mass spectrometry was modified with regard to the fatty acid composition and tritiated in the sphingosine base. These analogues were administrated intraperitoneally to diabetic ob/ob mice and their uptake in liver and pancreas analyzed after lipid extraction of dissected organs. The aim was to explore whether the exogenously administrated sulfatide was taken up by pancreas and thereby open a possibility to substitute for the quantitative and qualitative alterations of sulfatide seen in the diabetes type 2 models.

Radiolabeling of Sulfatide

Sulfatide was tritium labeled in the ceramide portion by catalytic hydrogenation with $Pd(OAc)_2/NaB^3H_4$. The labeled sulfatide was mixed with unlabelled sulfatide to the required specific activity.

Modification of the Fatty Acid Moiety in Sulfatide

The fatty acid was removed from native pig brain sulfatide by weak alkaline methanolysis at 80° C. The formed lysosulfatide was, after chromatographic purification, reacylated with respective fatty acid chloride in aqueous sodium acetate-tetrahydrofuran.

Administration of Radiolabeled Sulfatide Analogues to ob/ob Mice

The different sulfatide analogues, as shown in Table 2, were dissolved in phosphate buffered saline, 150 nmol/300 µL, (the samples were sonicated for 20 s) and then administrated i.p. to ob/ob mice. These mice were 12 weeks old and the mean value of the highest blood glucose was 13.4±1.3 nM. At sacrifice the mice were anaesthetized with $CO_2$ and killed by dislocation of the neck vertebrae. This is outlined in Table 2. The liver and pancreas were dissected immediately. The organ were quick-frozen and thawed at analyses (within 4 days).

TABLE 2

| Analogue of sulfatide | Nmol analogue given i.p. in each mouse | CPM given i.p. in each mouse | Mice sacrificed 6 h after i.p.; No. of mice | Mice sacrificed 24 h after i.p.; No. of mice |
|---|---|---|---|---|
| C8 | 150 | $5 \times 10^6$ | 2 | 2 |
| C16 | 150 | $3.5 \times 10^6$ | 2 | 2 |
| C24 | 150 | $2 \times 10^6$ | 2 | 2 |

Sulfatide Extraction and Analyses

The organs were homogenized and the lipids extracted with chloroform/methanol/water. The lipid extracts were evaporated, re-dissolved in chloroform/methanol/water and separated by silica gel chromatography to remove other lipids. The sulfatide containing fraction was used for counting by scintillation.

Figure 6A:
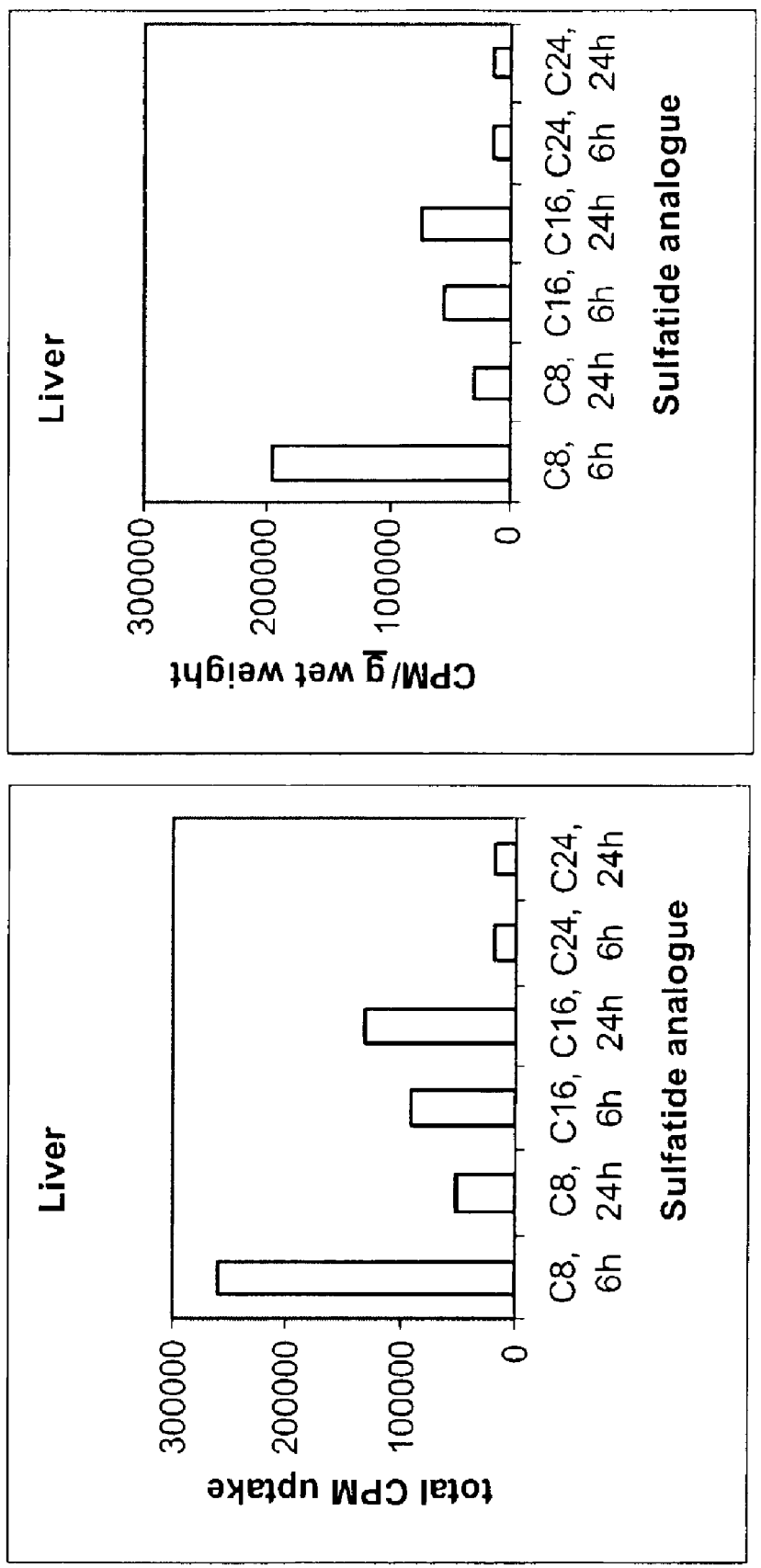
FIG. 6A illustrates the uptake of different sulfatide isoforms in liver.
Figure 6A:
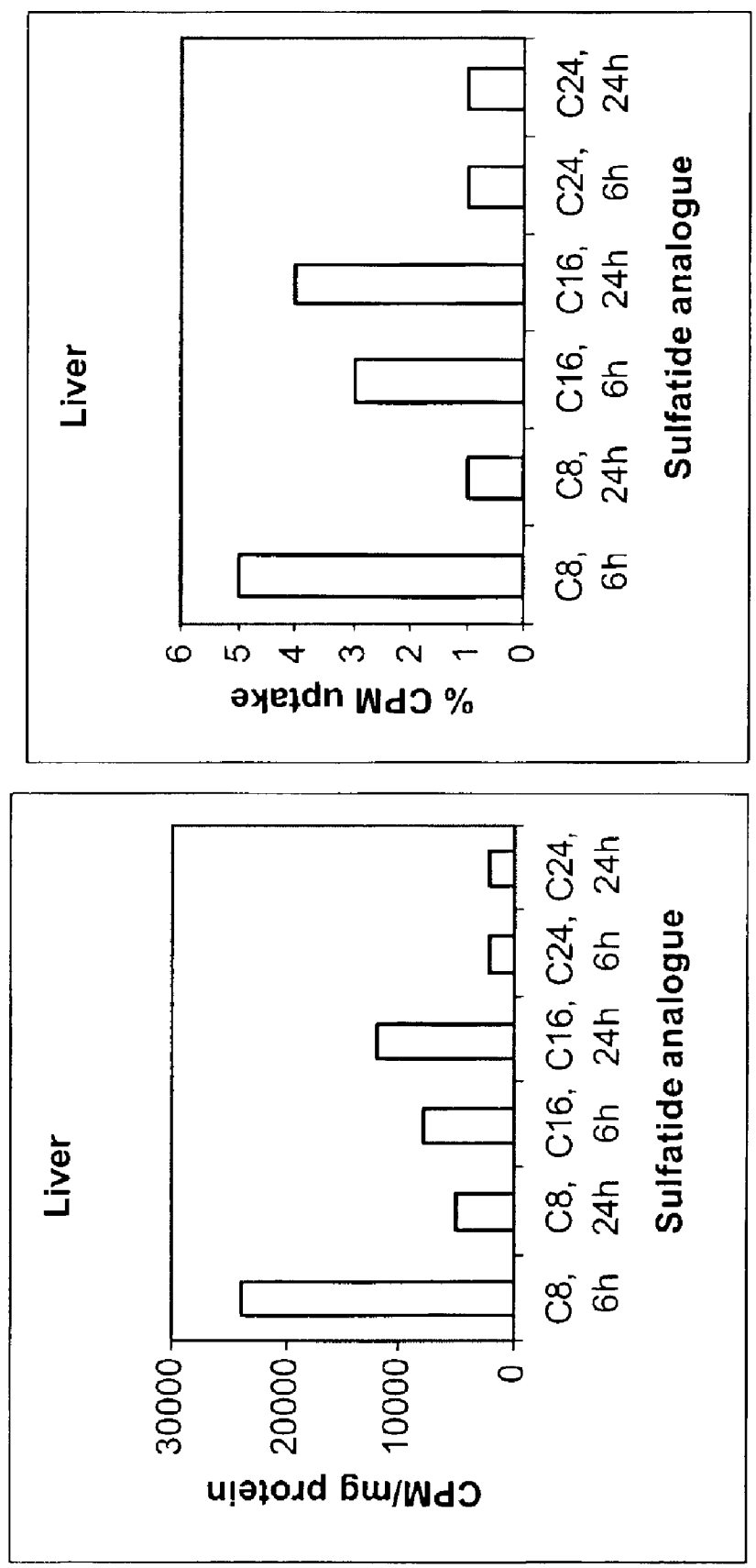
Figure 6A:
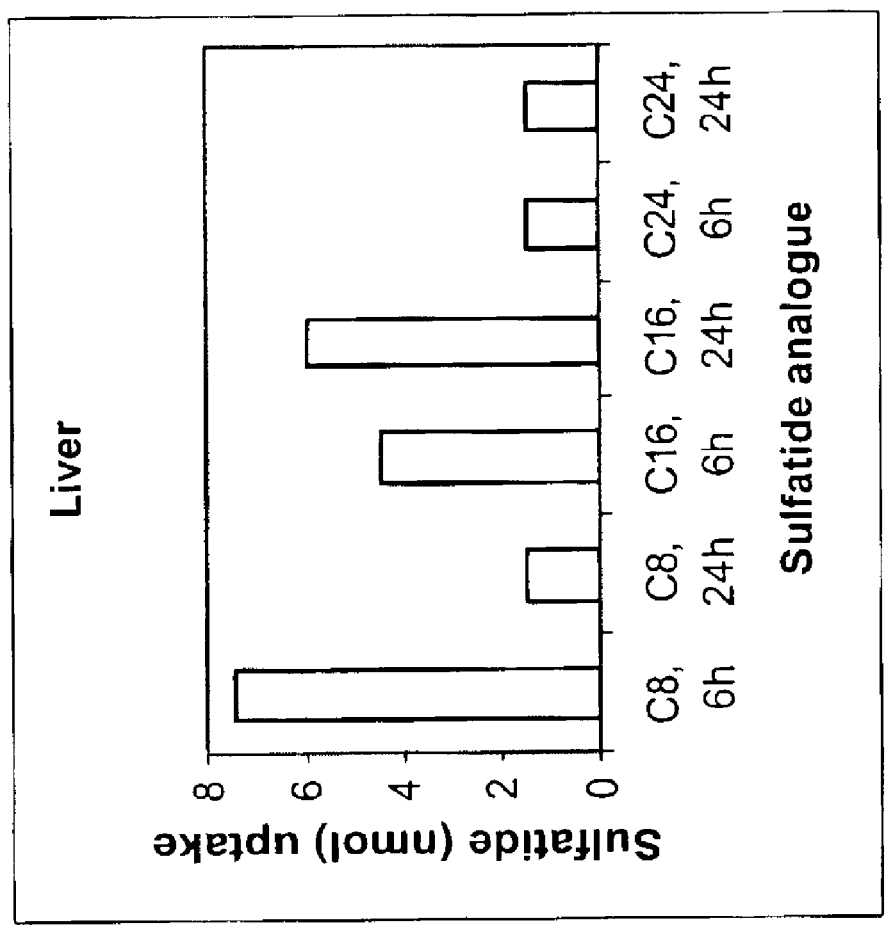
Figure 6B:
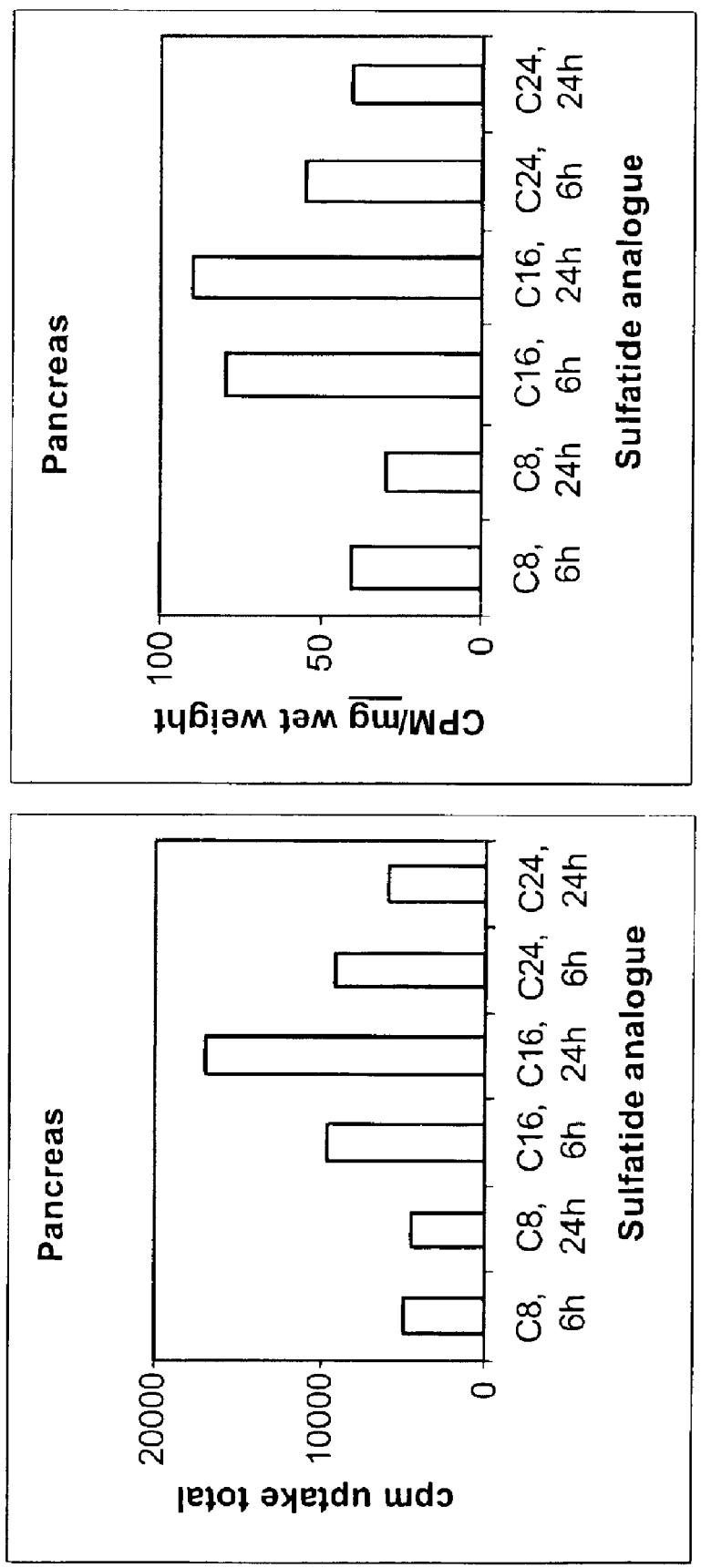
FIG. 6B illustrates the uptake of different sulfatide isoforms in pancreas.
Figure 6B:
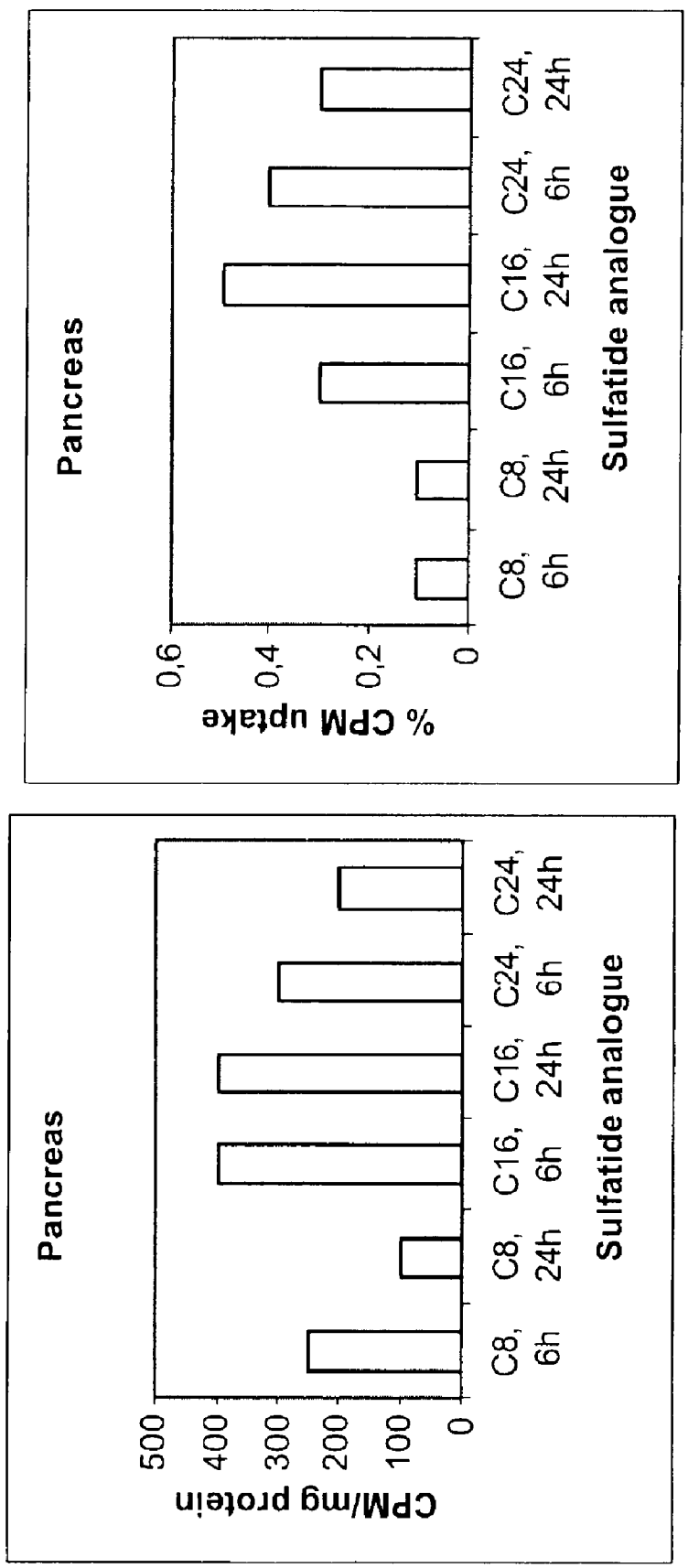
Figure 6B:
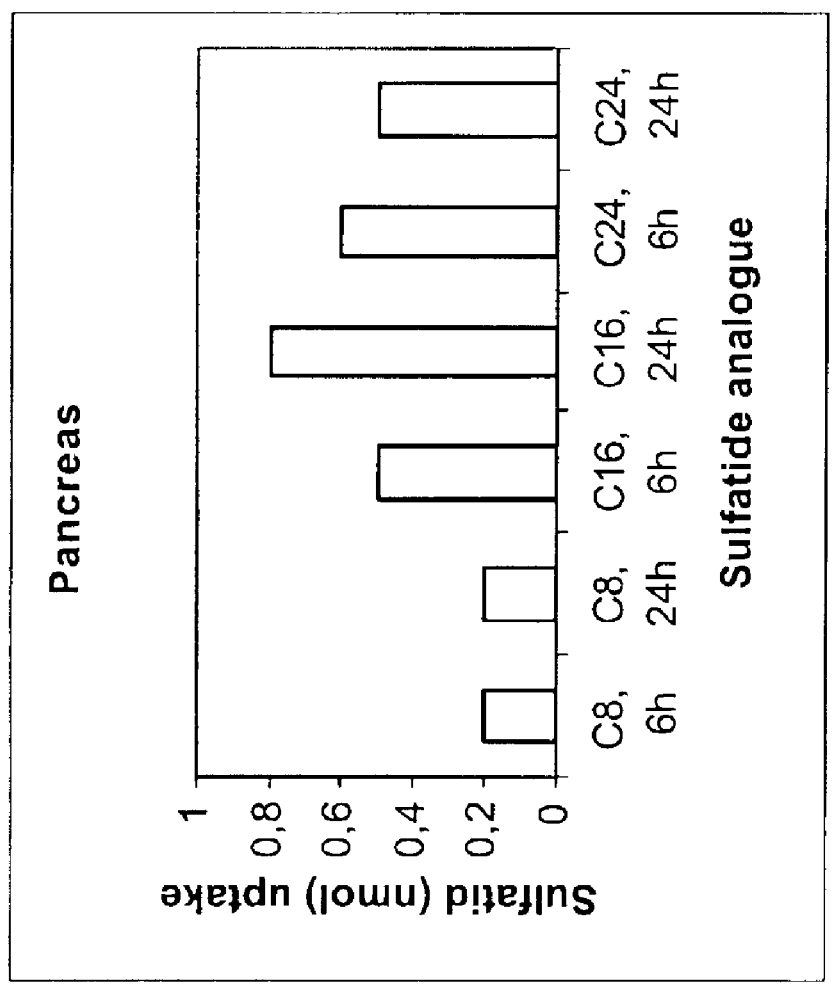
Figure 7:
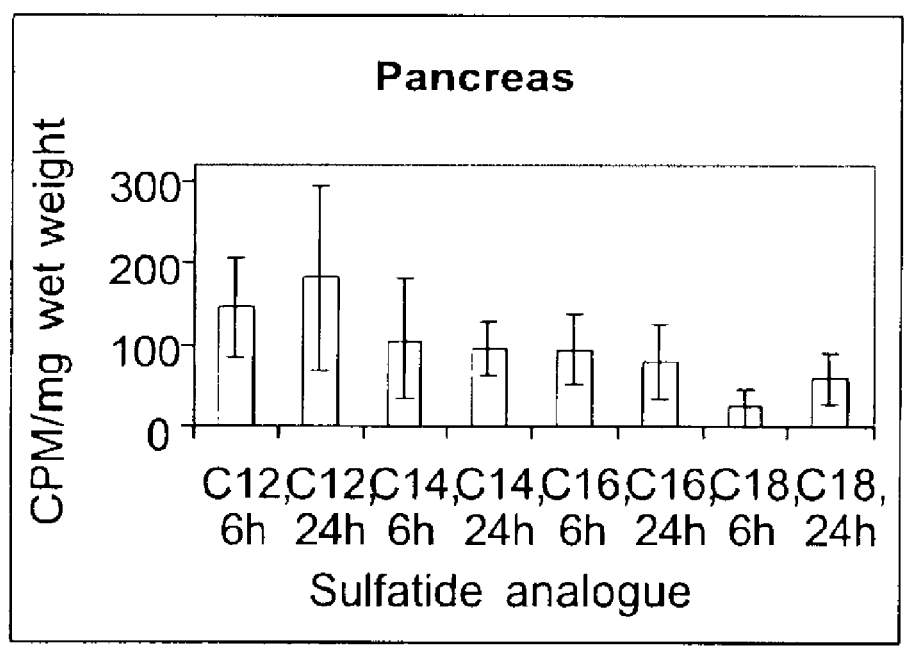
FIG. 7 illustrates the uptake of different sulfatide isoforms in pancreas.
Figure 8:
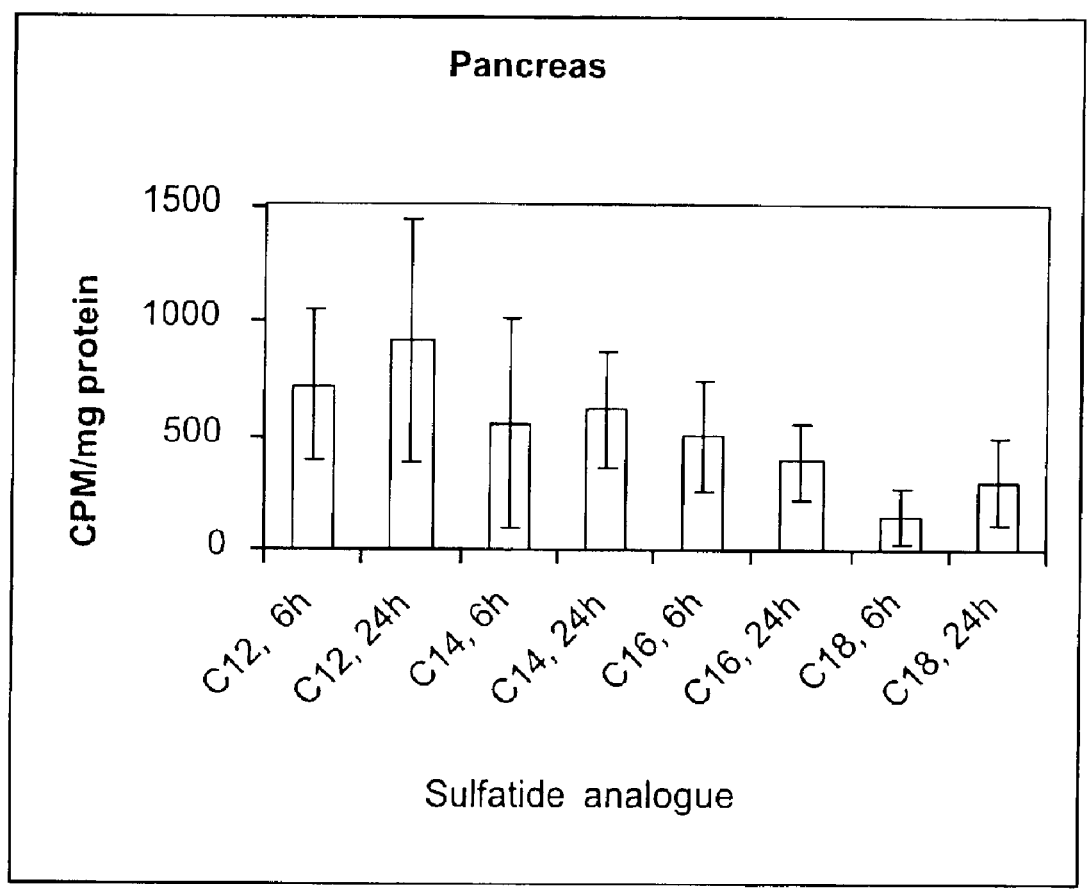
FIG. 8 illustrates the uptake of different sulfatide isoforms in pancreas.
Figure 9:
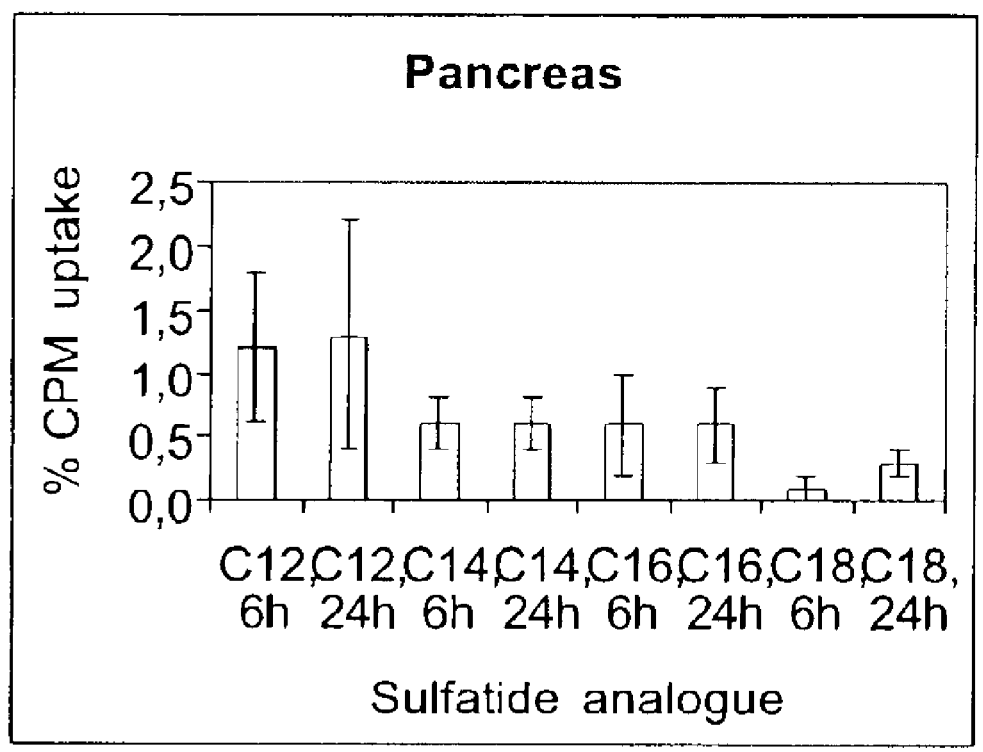
FIG. 9 illustrates the uptake of different sulfatide isoforms in pancreas.
Figure 10:
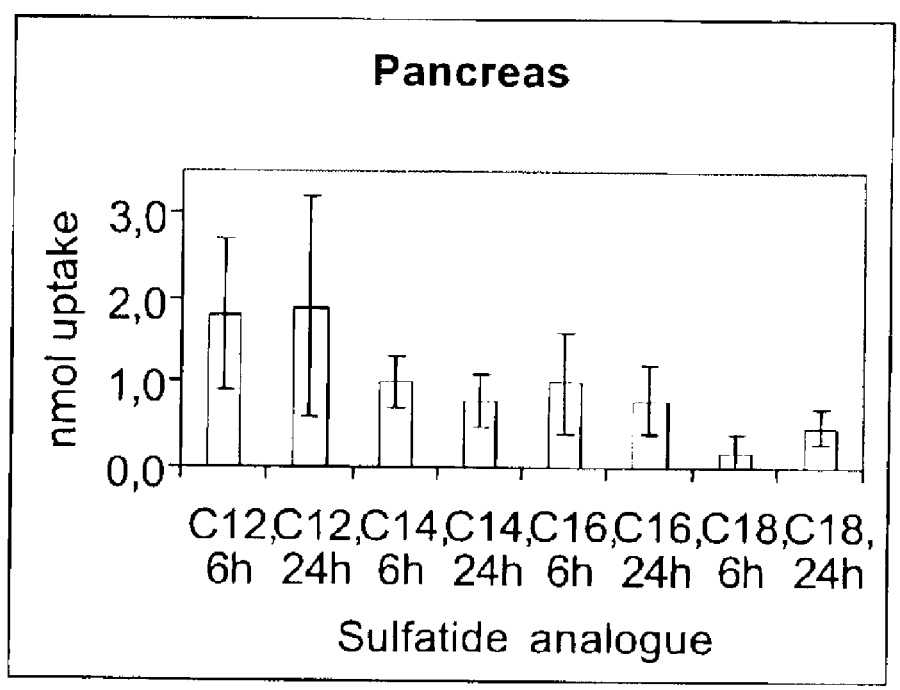
FIG. 10 illustrates the uptake of different sulfatide isoforms in pancreas.

The results of the scintillation measurement are presented in FIG. 6A and FIG. 6B—FIG. 6A presenting liver data and FIG. 6B pancreas data—as cpm uptake in total, cpm/mg wet weight of tissue, cpm/mg of tissue protein and % of given cpm residing in the organ The C8:0 analogue was preferentially taken up in liver and was rapidly degraded. In pancreas its uptake was much lower than for the other two analogues. The 6 hour and 24 hour value were similar and thus neither accumulation or degradation was noticed. The C24:0 analogue showed a lower uptake in liver as compared to the C8:0 analogue. There was a slight reduction of C24:0 in both organs at 24 hour indicating a slow degradation and no accumulation. The C16:0 analogue uptake in the liver was higher than for the C24:0 and also showed a slight accumulation. In comparison to the C8:0 analogue the liver uptake at 6 hours after administration was lower but in contrast to the finding with the C8:0 sulfatide, which was rapidly degraded, the C16:0 showed an accumulation at 24 hours. In pancreas the C16:0 sulfatide analogue was that most efficiently taken up and there was, like in liver, an accumulation after 24 hours.

Conclusion

The uptake of sulfatide varied between the analogues with different fatty acid composition. Among these the shortest C8:0 is rapidly removed from circulation to the liver and degraded. Moreover there was relatively uptake in pancreas and no accumulation. Both C16 and C24 analogues were efficiently taken up in pancreas but while C24 showed a slight degradation during the 24 hour period there was an accumulation of the C 16 analogue.

Thus, pancreas seems to have a selected uptake of the analogue of sulfatide that has been shown to be lacking in the diabetes type 2 models and thus the inventors have shown that administration of sulfatide, and especially the administration of the sulfatide isoform with 16 carbon atoms in the fatty acid is one way to restore the aberrant metabolism of this molecule.

EXAMPLE 3

Further Studies on the Uptake of Sulfatide in Pancreas and Liver in ob/ob Mice after Intraperiotenal Injection These experiments were performed as in Example 3, but only the uptake in pancreas was studies.

ob/ob mice was thus given C12, C14, C16 och C18 analogues of sulfatide intraperitoneally in the way described above.

The results are illustrated in FIGS. 7–10.

Conclusion

The uptake of sulfatide varied between the analogues with different fatty acid composition. Among these the C12, C14 and C16 give the most interesting results.

What is claimed is:

1. A method for treatment of a diabetic condition in a patient in need thereof, wherein a therapeutically effective amount of at least one isoform of sulfatide is administered to the patient in need thereof, and wherein said sulfatide isoform has a fatty acid with 12, 14 or 16 carbon atoms.

2. The method of claim 1, wherein said diabetic condition is pre-diabetes, diabetes, glucose intolerance, and/or insulin resistance.

3. The method of claim 2, wherein said diabetes is diabetes type 1, diabetes type 2, latent autoimmune diabetes in adults (LADA), and/or gestational diabetes.

4. The method of claim 3, wherein said diabetes is diabetes type 2.

5. The method of claim 1, wherein only one isoform of sulfatide is used.

6. The method of claim 2, wherein only one isoform of sulfatide is used.

7. The method of claim 3, wherein only one isoform of sulfatide is used.

8. The method of claim 4, wherein only one isoform of sulfatide is used.

9. The method of claim 1, wherein said at least one isoform of sulfatide comprises no double bonds in its fatty acid chain.

10. The method of claim 2, wherein said at least one isoform of sulfatide comprises no double bonds in its fatty acid chain.

11. The method of claim 3, wherein said at least one isoform of sulfatide comprises no double bonds in its fatty acid chain.

12. The method of claim 4, wherein said at least one isoform of sulfatide comprises no double bonds in its fatty acid chain.

13. The method of claim 1, wherein said at least one isoform of sulfatide is administered orally.

14. The method of claim 2, wherein said at least one isoform of sulfatide is administered orally.

15. The method of claim 3, wherein said at least one isoform of sulfatide is administered orally.

16. The method of claim 4, wherein said at least one isoform of sulfatide is administered orally.

17. A method for treatment of a diabetic condition in a patient in need thereof, wherein a therapeutically effective amount of an isoform of sulfatide is administered to the patient in need thereof, and wherein said sulfatide isoform has a fatty acid with 16 carbon atoms.

18. The method of claim 17, wherein said isoform of sulfatide comprises no double bonds in its fatty acid chain.

19. The method of claim 17, wherein said isoform of sulfatide is administered orally.

20. A method of producing a pharmaceutical composition for treating a diabetic condition, comprising admixing at least one sulfatide isoform with a pharmaceutically acceptable adjuvant, carrier and/or preservative, and wherein said sulfatide isoform has a fatty acid with 12, 14 or 16 carbon atoms.

21. The method of claim 20, wherein only one isoform of sulfatide is used.

22. The method of claim 20, wherein said at least one isoform of sulfatide comprises no double bonds in its fatty acid chain.

23. The method of claim 20, wherein said pharmaceutical composition is formulated for oral administration.

24. The method of claim 20, wherein a substrate used to facilitate the production of the preparation is selected from the group consisting of pharmaceutically acceptable adjuvants, carriers and preservatives.

25. A method of producing a pharmaceutical composition for treating a diabetic condition, comprising admixing a sulfatide isoform with a pharmaceutically acceptable adjuvant, carrier and/or preservative, and wherein said sulfatide isoform has a fatty acid with 16 carbon atoms.

26. The method of claim 25, wherein said isoform of sulfatide comprises no double bonds in its fatty acid chain.

27. The method of claim 25, wherein said pharmaceutical composition is formulated for oral administration.

* * * * *